United States Patent [19]
Pless et al.

[11] Patent Number: 5,922,215
[45] Date of Patent: Jul. 13, 1999

[54] METHOD FOR MAKING ANODE FOIL FOR LAYERED ELECTROLYTIC CAPACITOR AND CAPACITOR MADE THEREWITH

[75] Inventors: Benjamin D. Pless, Atherton, Calif.; William H. Elias, Six Mile, S.C.; Sam Parler, Clemson, S.C.; J. Scott McCall, Six Mile, S.C.

[73] Assignee: Pacesetter, Inc., Sunnyvale, Calif.

[21] Appl. No.: 08/732,651

[22] Filed: Oct. 15, 1996

[51] Int. Cl.$^6$ ................................. B44C 1/22; C23F 1/00
[52] U.S. Cl. ................... 216/6; 216/33; 216/102; 216/52; 361/522; 361/529
[58] Field of Search .................. 216/6, 33, 41, 216/52–102; 361/517, 522, 523, 529, 535, 541

[56] References Cited

U.S. PATENT DOCUMENTS

| | | | |
|---|---|---|---|
| 3,365,378 | 1/1968 | Maissel et al. | 216/6 X |
| 3,997,812 | 12/1976 | Stahle et al. | 313/458 |
| 4,484,252 | 11/1984 | Ruijgrok et al. | 361/433 |
| 4,518,471 | 5/1985 | Arora | 204/129 |
| 4,827,381 | 5/1989 | Brommer et al. | 361/531 |
| 4,942,501 | 7/1990 | MacFarlane et al. | 361/523 |
| 5,131,388 | 7/1992 | Pless et al. | 128/419 |
| 5,522,851 | 6/1996 | Fayram | 607/5 |
| 5,660,737 | 8/1997 | Elias et al. | 216/6 |

*Primary Examiner*—William Powell
*Attorney, Agent, or Firm*—Steven M. Mitchell

[57] ABSTRACT

A method for making anode foil plates for use with layered electrolytic capacitors and capacitors made with such plates. A high purity aluminum foil is provided for generation of anode foil plates. Sheets of the foil are highly etched to provide a very high surface area. Following the etch process, the foil is partially cut or punched into plates from the etched sheets in the general shape of the finished capacitor housing with a portion remaining connected to the supporting foil. The supporting foil with the partially punched-out etched plates are subjected to a forming process by applying a voltage to the plates in the presence of an electrolyte to provide formed anode foil plates with edges which do not have to be reformed during capacitor aging and which do not have any particulates at cut edges. The formed anode plates are layered with cathode plates and separators in a capacitor housing with an electrolyte to provide a finished capacitor.

17 Claims, 3 Drawing Sheets

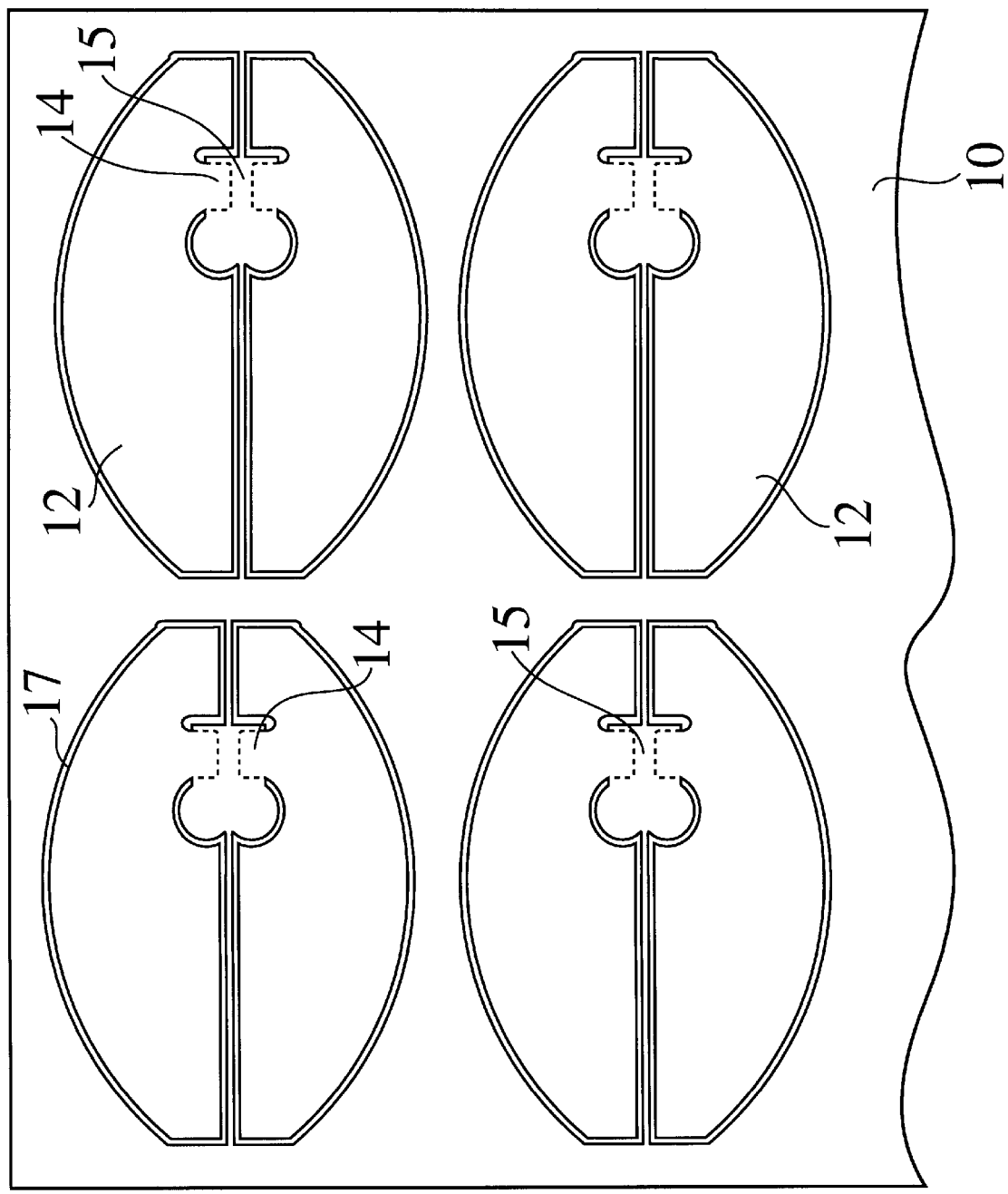

METHOD FOR MAKING ANODE FOIL FOR LAYERED ELECTROLYTIC CAPACITOR AND CAPACITOR MADE THEREWITH

FIELD OF THE INVENTION

The present invention relates generally to aluminum electrolytic capacitors, and more specifically to a method for making an improved anode foil for layered aluminum electrolytic capacitors.

BACKGROUND OF THE INVENTION

High-voltage capacitors are useful in technology applications where brief high-voltage pulses must be delivered, for example, in automatic implantable cardioverter/defibrillators ("ICDs") where high-voltage pulses are required across the defibrillation lead system to affect defibrillation or cardioversion. An ICD and package therefor, including rolled (or "wound") capacitors, are described in U.S. Pat. No. 4,254,775 to Langer.

Typically, electrolytic capacitors are used in these applications because they have the best properties in terms of energy density and ability to withstand relatively high voltage. Aluminum electrolytic capacitors are generally used, having aluminum foil rolled into a small volume in the form of a cylinder. By etching the surface of the aluminum foil prior to rolling, the surface area and the capacitance are increased accordingly. In the case of such rolled or cylindrical aluminum electrolytic capacitor, the foil is etched, then formed to provide an oxide layer which functions as the dielectric for the capacitor. The formed foil is rolled and then "aged" in the presence of an electrolyte to grow oxide on any exposed aluminum. Aging is the process of slowly increasing the voltage on the capacitor after impregnation with electrolyte over the course of many hours by charging the capacitor using a small current source. After reaching the maximum rated voltage, the voltage may be decreased and the temperature increased. Further details of the construction of such traditional high voltage capacitors used in ICDs are described by P. J. Troup, "Implantable Cardioverters and Defibrillators," at pp. 704–713 (*Current Problems in Cardiology*, Vol. XIV, No. 12, December 1989, Year Book Medical Publishers, Chicago), which pages are incorporated herein by reference.

In implantable defibrillators, as in other applications where space is a critical design element it is desirable to use capacitors with the greatest possible capacitance per unit volume. One problem with cylindrical aluminum electrolytic capacitors is that the foil cannot be etched as much as might be desirable because heavily etched and formed foils are very fragile and may break during the rolling step. Additionally, the cylindrical shape does not provide an optimum device for packaging of the ICD. One way to allow increased etching of the foil and thus increase capacitance per unit area is to construct the capacitor in a flat, layered or stacked configuration with very highly etched anode foil. This also allows the ICD designer to select the general profile of the capacitor. An implantable cardiac defibrillator with improved flat capacitors is described in U.S. Pat. No. 5,131,388 to Pless et al., which patent is incorporated herein by reference.

For layered capacitors, after the foil is etched, voltage is applied to the foil through an electrolyte such as boric acid or citric acid and water or other solutions familiar to those skilled in the state of the art, resulting in the formation of aluminum oxide ($Al_2O_3$) on the surface of the anode foil. Following formation of the oxide on the foil, individual anode plates are punched, stamped or otherwise cut out of the foil in a shape to conform to the capacitor package. The cut edges around the periphery of the anode plates are carefully cleaned to remove particulates of anode material that can get caught between the capacitor plates in the stacked configuration resulting in a high leakage current or capacitor failure. After assembling the capacitor by stacking anode plates, paper and cathode foil, the cut edges of the plates and any other exposed aluminum are then reformed in the capacitor during the aging process to reduce leakage current. However, the oxide produced at the edges during reforming is not as good a quality as the original oxide due to process differences.

It is therefore an object of the present invention to provide a capacitor anode foil plate that does not suffer from the above drawbacks.

It is another object of the invention to provide a method of making a capacitor anode foil plate having a high quality oxide layer at the plate edges.

It is still another object of the invention provide an anode plate which improves the manufacturability and performance of layered aluminum electrolytic capacitors.

SUMMARY OF THE INVENTION

The instant invention is directed to a method for making anode foil plates for use with layered electrolytic capacitors and capacitors made with such plates. In a preferred embodiment of the invention, a high purity aluminum foil is provided for generation of anode foil plates. Sheets of the foil are highly etched with portions of the foil masked to provide unetched or reduced etch tabs. Following the etch process, the foil is cut or punched into plates from the etched sheets in the general shape of the finished capacitor housing, preferably still attached by the tabs to the foil sheet to provide support and ease of handling. After the etched plates are punched out, they are formed by applying a voltage to the plates in the presence of an electrolyte to provide formed anode foil plates which do not have to be reformed during capacitor aging and which do not generate particulate matter at cut edges. The formed anode plates are layered with cathode plates and paper separators in a capacitor housing with an electrolyte to provide a finished capacitor.

A benefit of the process of the invention is that the energy costs associated with forming the anode foil may be reduced because only foil that will be used in the capacitor need be formed. The time to produce the foil is decreased because of the reduced anode area during formation. The resulting anode plates are ready to be assembled into capacitors, which reduces labor by eliminating the need to clean the cut edges. Aging of the capacitor may be accomplished more quickly because the cut edges of the anodes do not need to be reformed in the capacitor during the aging process. Capacitor performance is improved because all of the anode oxide is of high quality which reduces leakage current in the finished device. Reliability is improved because there is less particulate matter in the capacitor. Energy density can be improved because thinner paper separators can be used between the layers since there is less particulate matter on the anode plate edges.

BRIEF DESCRIPTION OF THE DRAWINGS

The various features and advantages of the present invention may be more readily understood with reference to the following detailed description taken in conjunction with the accompanying drawings in which:

FIG. 2 is a plan view of a foil sheet showing a plurality of plates partially punched from the sheet;

DETAILED DESCRIPTION OF THE INVENTION

Figure 1:
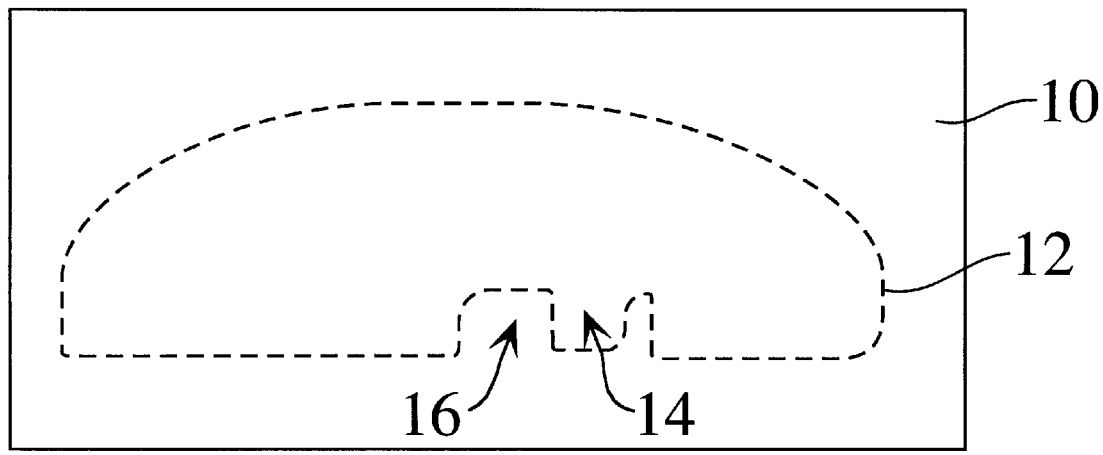
FIG. 1 is a plan view of an etched anode foil illustrating the plate periphery which is to be cut from the foil.

Referring now to FIG. 1, a plan view of an etched anode foil for a flat layered capacitor is shown. In the preferred embodiment, an aluminum anode foil sheet 10 is about 2 to 10 mils thick. A phantom outline of an anode plate 12 is shown illustrating the cut or punch lines for the plate 12. As used herein cutting and punching are intended to include any means for separating the plates from the foil such as stamping, abrading or other known techniques. FIG. 1 shows a foil with a single anode plate for illustration purposes and it will be understood that a larger area foil is generally preferable with a plurality of plates punched from each foil as will be discussed below with reference to FIG. 2. The foil sheet 10 has been etched, preferably in accordance with the procedure described in co-pending U.S. patent application Ser. No. 08/443,134, filed May 17, 1995, U.S. Pat. No. 5,660,737, which is incorporated herein by reference. As described therein, a tab portion 14 and possibly an area around the periphery of anode plate 12 are masked during the etch process to provide portions of the foil which are unetched. The plate is cut in the general shape of the capacitor housing and includes anode tab portion 14 and a cutout portion 16 into which cathode plate tabs will extend in a layered capacitor. Thus, the surface of plate 12 except tab 14 is etched and the area of foil 10 outside the plate 12 may be etched or may be masked during the etch process and remain unetched. In the layered capacitor, the anode tabs are welded together and connected to a feedthrough in the capacitor housing to provide the anode electrode connection to the capacitor. The cathode tabs are ultrasonically welded together and to the capacitor case. The capacitor housing is configured to conform to a defibrillator housing. However, any other desired shape could be used. The anode plates of the invention can also be used with solid electrolyte capacitors where no capacitor case is required such as described in U.S. Pat. No. 4,942,501 "Solid Electrolyte Capacitors and Methods of Making the Same" to MacFarlane et al., which patent is incorporated herein by reference.

Referring now to FIG. 2, a foil sheet 10 is shown having a plurality of partially punched out anode plates 12 with pairs of plates connected to the foil sheet 10 and to each other by an unetched tab bridge 15. A punched-out outline 17 is shown around the periphery of each plate 12 except for the tab bridges 15. Anode tabs 14 are shown in phantom outline. The remaining portion of foil sheet 10 may be etched or unetched as discussed above and serves to support the plates 12. Leaving this portion of foil sheet 10 unetched reduces the current required for forming the anode plates. After the forming step, the plates 12 may be cut from foil sheet 10 along tab bridge 15 which is trimmed to produce tabs 14.

Figure 3:
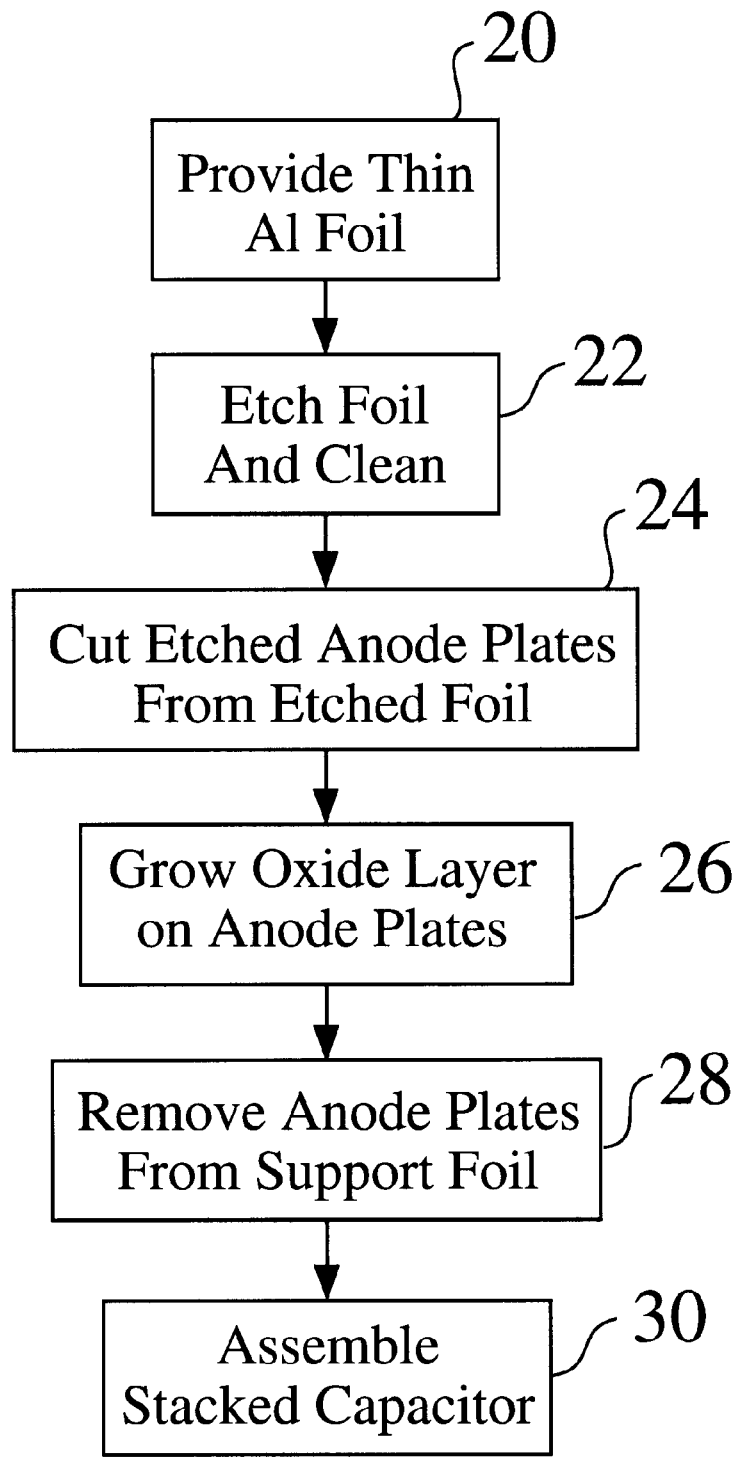
FIG. 3 is a process diagram illustrating the steps of the invention in producing improved anode plates and capacitor.

Referring now to FIG. 3, a process diagram illustrating the steps of the invention in producing the anode plates and capacitor is shown. A sheet of thin high purity aluminum foil is provided at step 20. As mentioned above, the foil is about 2 to 10 mils thick. The foil is then highly etched and cleaned at step 22. The etch process including masking portions of the anode plate is described in U.S. patent application Ser. No. 08/443,134. For purposes of the present invention, other etch processes known in the art could be used and the particular etch process used is not a part of the present invention. The etched foil may be cleaned with water. After the foil 10 is etched and cleaned, the anode plates 12 are stamped from the foil at step 24 using conventional matched metal dies. The anode plate 10 is now ready for forming which involves growing an oxide layer on the etched surface at step 26. This is typically done by applying a voltage to the foil through an electrolyte such as boric acid or citric acid and water or other solutions familiar to those skilled in the art, resulting in the formation of aluminum oxide ($Al_2O_3$) on the surface of the anode plate 10. The thickness of aluminum oxide deposited or "formed" on the anode foil is proportional to the applied voltage. A benefit of the invention is that the edges are formed in this forming process step rather than the aging process step resulting in a higher quality oxide layer at the edges. If the anode plates 12 were left attached to the foil sheet 10 for the forming process, the plates are removed from the supporting foil at step 28 and the tabs 14 are trimmed. A plurality of these anode plates are assembled with cathode plates and separators into a stacked or layered capacitor assembly at step 30 which is then placed in a capacitor case into which an electrolyte is introduced. Alternatively, the assembly step may be performed by placing the various layers directly into a portion of the capacitor housing which is later closed. Such an assembly method is described in U.S. Pat. No. 5,522,851, to Fayram, which patent is incorporated herein by reference. Alternatively, a capacitor housing may not be required when using a solid electrolyte as discussed above.

Figure 4:
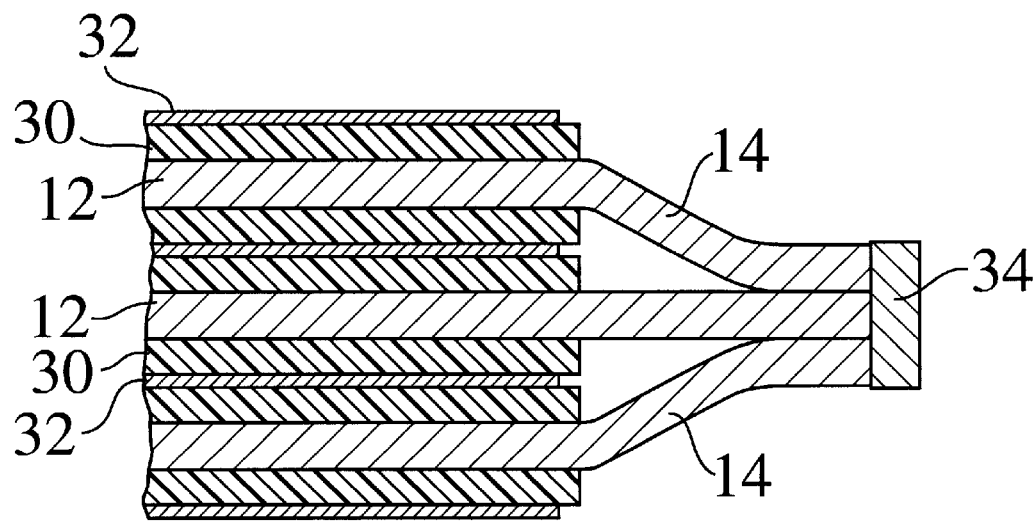
FIG. 4 illustrates a partial cross section of a layered capacitor of the invention.

FIG. 4 shows a cross-sectional view of a portion of a stacked flat capacitor. Each anode plate 12 of the stack has been highly etched on both sides. Each capacitor anode layer may consist of a single anode plate 12, double anode plates, or a higher number of anode plates. Each configuration will give a different energy density and different ESR. ESR is the capacitor series resistance which should be as low as possible or at least matched to the application. Energy density gets better as the number of anode plates per layer increases, but ESR gets worse (i.e., gets higher). The actual number of anode plates per layer will therefore be a compromise between a lower energy density and an acceptable ESR, with two anode plates in common use for these and similar applications. Paper separators 30 cover each anode layer and separate each anode layer from adjacent cathode plates 32. Only three layers of anode plates have been shown for illustrative purposes but the actual number of layers used will be a function of the anode area and the desired capacitance of the finished capacitor. Upper and lower weld tabs 14 are shown bending toward a center tab. A riser 34 of high purity aluminum is placed at the ends of the tabs and joined perpendicular to them. Two laser welds are made along the face of the tabs at each side of the riser joining the plates as well as connecting them to the riser. The riser will be connected to an anode terminal when the plates are assembled in a capacitor housing. Cathode plates 32 have similar tabs that are joined together and welded directly to the case by ultrasonic welding.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A process for making an anode foil plate for use in an electrolytic capacitor comprising the steps of:

provided a thin metallic foil;

etching said foil to provide enhanced surface area;

following said etching step, cutting a shape in said foil to provide an etched anode foil plate; and following said cutting step, forming an oxide layer on said anode foil plate.

2. The process of claim 1 wherein said step of providing a metallic foil comprises providing an aluminum foil.

3. The process of claim 1 wherein said cutting step includes leaving a portion of said anode foil plate attached to said metallic foil.

4. The process of claim 1 wherein said cutting step includes cutting a plurality of shapes in said foil to provide a plurality of etched anode foil plates.

5. A process of making an electrolytic capacitor comprising the steps of:

preparing an anode foil by etching at least a portion of at least one major surface of said foil;

following said etching step, cutting a shape in said foil to provide an etched anode foil plate;

following said cutting step, growing an oxide layer on the etched portion of said anode foil plate;

providing a separator and a cathode foil; and assembling said separator between one surface of said anode foil and said cathode foil.

6. The method of claim 5 and further including the step of enclosing the assembly of said cathode, anode and separator in a housing.

7. The method of claim 6 and further including the step of impregnating said assembly with an electrolyte.

8. The method of claim 5 wherein said separator comprises a solid electrolyte.

9. The method of claim 5 further including the step of providing a plurality of anode foils positioned adjacent each other to provide an anode layer and wherein said assembling step includes assembling said separator between said anode layer and said cathode foil.

10. A layered aluminum electrolytic capacitor comprising:

an anode foil plate having opposing surfaces and edges around the periphery of said surfaces and having substantially uniform oxide layers formed across said surfaces and said edges;

a cathode foil;

a separator layer positioned between said anode foil and said cathode foil; and an electrolyte.

11. The capacitor of claim 10 wherein a plurality of anode foils, cathode foils and separator layers are stacked together to form a layered structure with said anode foils electrically coupled together and said cathode foils electrically coupled together.

12. The capacitor of claim 11 and further including:

a housing for enclosing said layered structure and said electrolyte;

an anode electrical contact extending from said coupled anode foils to outside said housing; and a cathode electrical contact extending from said coupled cathode foils to outside said housing.

13. The capacitor of claim 11 wherein multiple ones of said plurality of anode foils are positioned adjacent each other to form an anode layer and wherein said anode layer is positioned between respective adjacent separator layers.

14. The capacitor of claim 10 wherein said separator layer comprises a solid electrolyte.

15. A process of making an electrolytic capacitor comprising the steps of:

providing a thin aluminum foil and etching said foil;

cutting a plurality etched anode plates in said etched aluminum foil;

following said cutting step, growing oxide layers on said anode plates;

providing a plurality of separators and cathode plates; and assembling said plates and separators in a sequence of cathode plate, separator, anode layer, separator, cathode plate, separator;

wherein said anode layer includes one or more anode plates.

16. The method of claim 15 and further including the step of enclosing the assembly in a housing.

17. The method of claim 15 and further including the step of impregnating said capacitor with an electrolyte.

* * * * *